United States Patent
Kwon et al.

(10) Patent No.: US 12,377,417 B2
(45) Date of Patent: Aug. 5, 2025

(54) METHOD FOR ANALYSIS OF BIOSPECIMEN, ANALYSIS CHIP AND ANALYSIS SYSTEM BASED ON BIOREACTOR

(71) Applicant: METEOR BIOTECH, CO. LTD., Seoul (KR)

(72) Inventors: Sung Hoon Kwon, Seoul (KR); Ok Ju Kim, Seoul (KR); Jin Sung Noh, Seoul (KR); Yu Shin Jung, Seoul (KR); Tae Hoon Ryu, Gimpo-si (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 838 days.

(21) Appl. No.: 16/968,337

(22) PCT Filed: Feb. 8, 2019

(86) PCT No.: PCT/KR2019/001588
§ 371 (c)(1),
(2) Date: Aug. 7, 2020

(87) PCT Pub. No.: WO2019/156511
PCT Pub. Date: Aug. 15, 2019

(65) Prior Publication Data
US 2021/0094032 A1    Apr. 1, 2021

(30) Foreign Application Priority Data

Feb. 9, 2018 (KR) .......................... 10-2018-0016125

(51) Int. Cl.
*B01L 3/00* (2006.01)
(52) U.S. Cl.
CPC ... *B01L 3/50855* (2013.01); *B01L 2300/0829* (2013.01)

(58) Field of Classification Search
CPC ....... B01L 2200/0647; B01L 2300/087; B01L 2300/0816
(Continued)

(56) References Cited

U.S. PATENT DOCUMENTS 3,979,184 A * 9/1976 Giaever ................. G01N 21/45
422/429
2005/0272159 A1* 12/2005 Ismagilov ................. B01L 7/52
436/34

FOREIGN PATENT DOCUMENTS

JP     2010063395 A     3/2010
KR    100523767 B1    10/2005
(Continued)

OTHER PUBLICATIONS

International Search Report of PCT/KR2019/001588, May 27, 2019, English translation.
(Continued)

*Primary Examiner* — Natalia Levkovich
(74) *Attorney, Agent, or Firm* — STIP Law Group, LLC

(57) ABSTRACT

Provided are a method of analyzing biological samples, an analytical chip and an analytical system comprising same, the method comprising the steps of: introducing structures for assisting the formation of bioreactors on a substrate; providing a plurality of bioreactors on the substrate by means of forming the bioreactors, which are holding biological samples, on the peripheral parts of the respective structures so as to come in contact with the structures in at least one region; and checking a change in the biological samples present in the bioreactors.

19 Claims, 7 Drawing Sheets

(58) Field of Classification Search
USPC .................................................. 436/174, 53
See application file for complete search history.

(56) References Cited

FOREIGN PATENT DOCUMENTS

| KR | 1020160019913 A | 2/2016 |
|---|---|---|
| KR | 1020170047182 A | 5/2017 |

OTHER PUBLICATIONS

Yang Yang et al., 3D-Printed Biomimetic Super-Hydrophobic Structure for Microdroplet Manipulation and Oil/Water Separation, Advanced Materials, 2018, vol. 30, No. 1704912 , Wiley-VCH Verlag Gmbh & Co. KGaA, Weinheim, Germany.
David K. Wood et al., Single cell trapping and DNA damage analysis using microwell arrays, PNAS, Jun. 1, 2010, vol. 107, No. 22, pp. 10008-10013, PNAS, Washington D.C , USA.

* cited by examiner

[Figure 1]
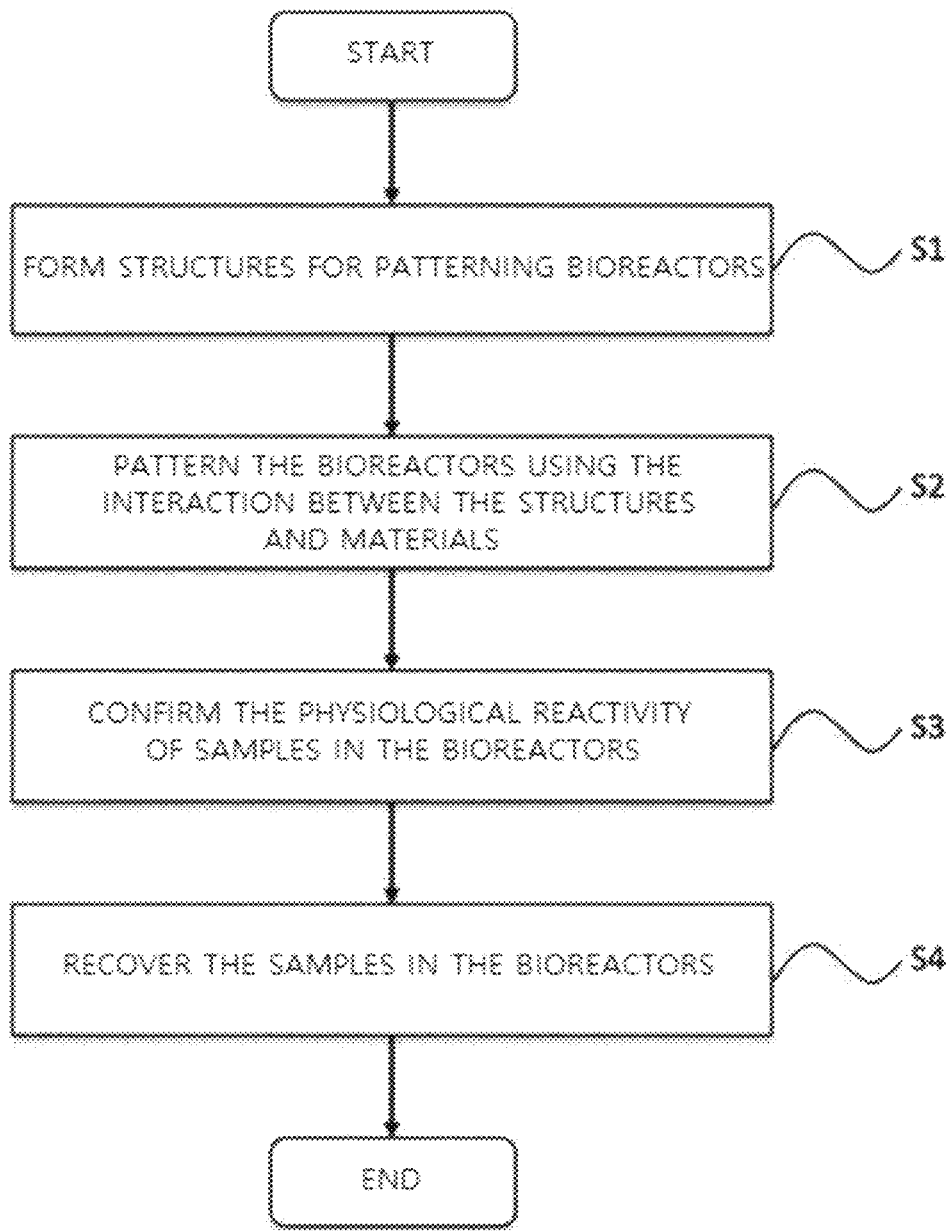

[Figure 2(a)]
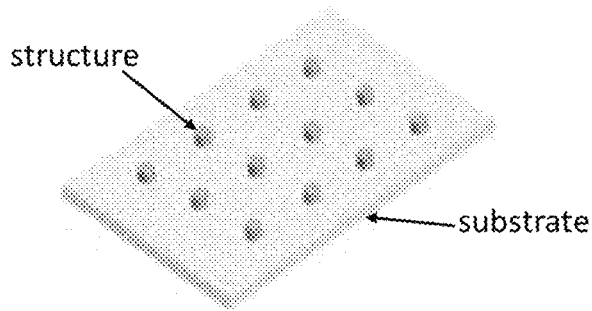
(a) FORMATION OF STRUCTURES
[Figure 2(b)]
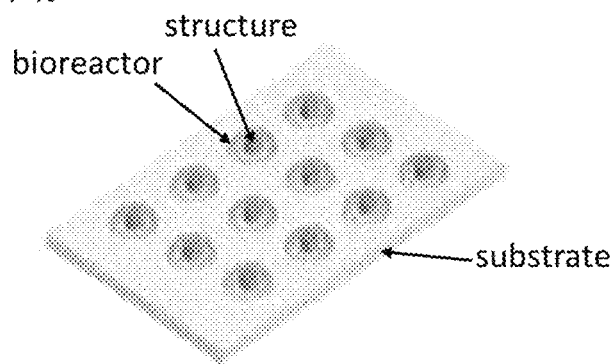
(b) PATTERNING OF BIOREACTORS
[Figure 2(c)]
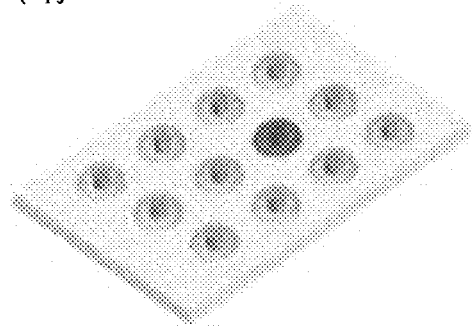
(c) SCREENING OF BIOREACTORS 【Figure 2(d)】
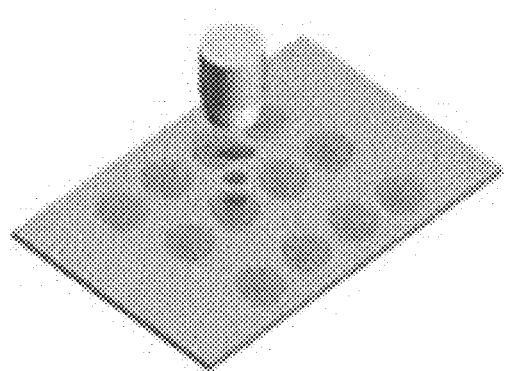
(d) RECOVERING OF SAMPLE
【Figure 3】
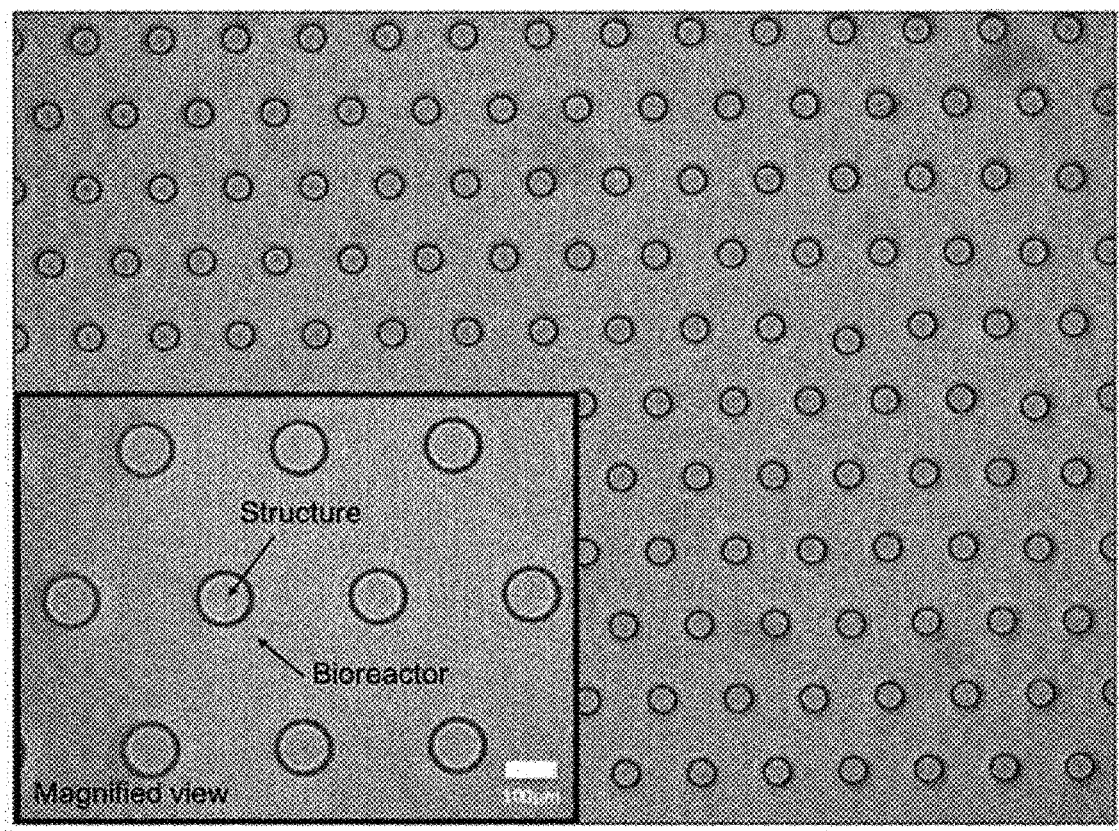

[Figure 4]
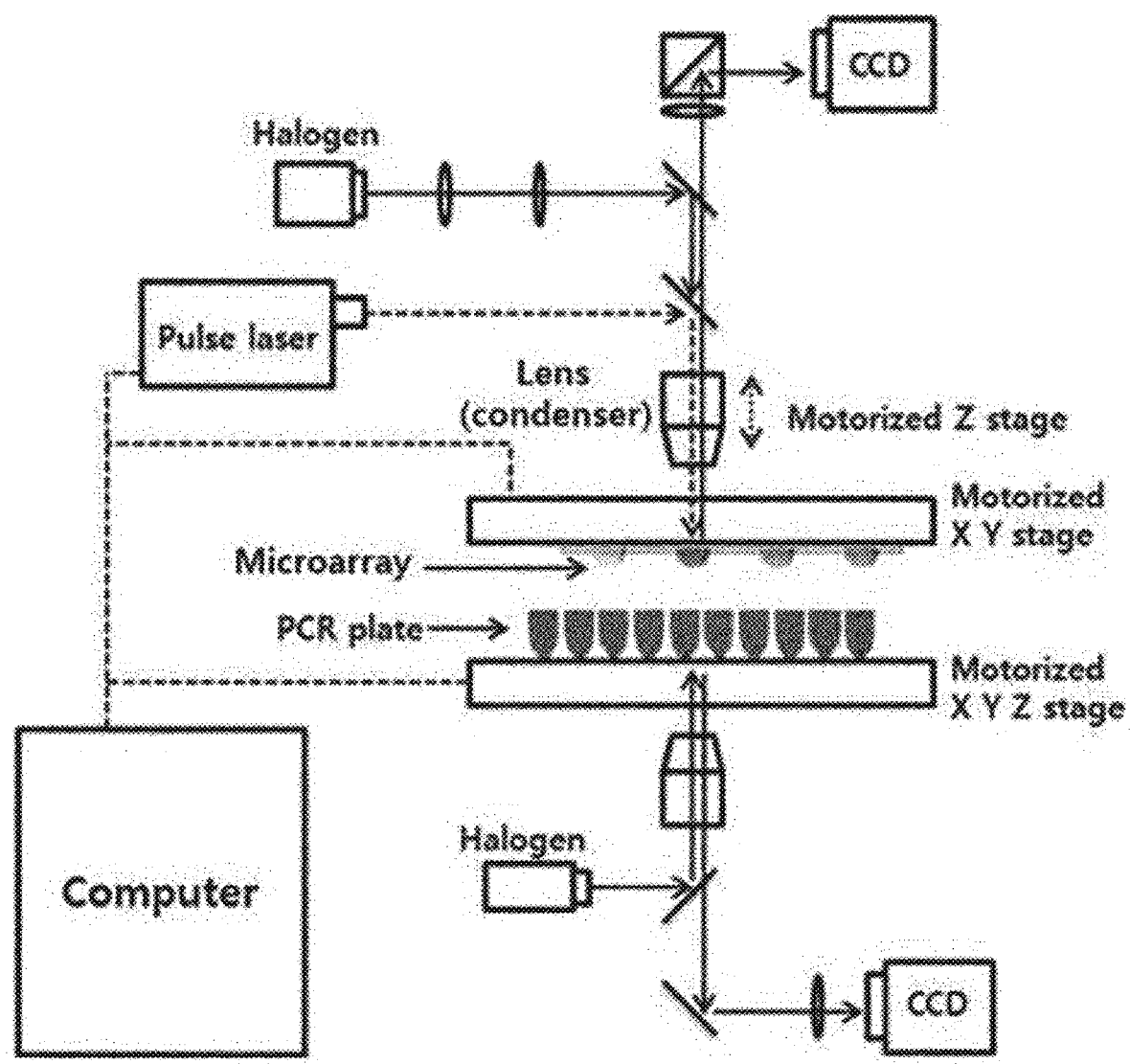

[Figure 5]
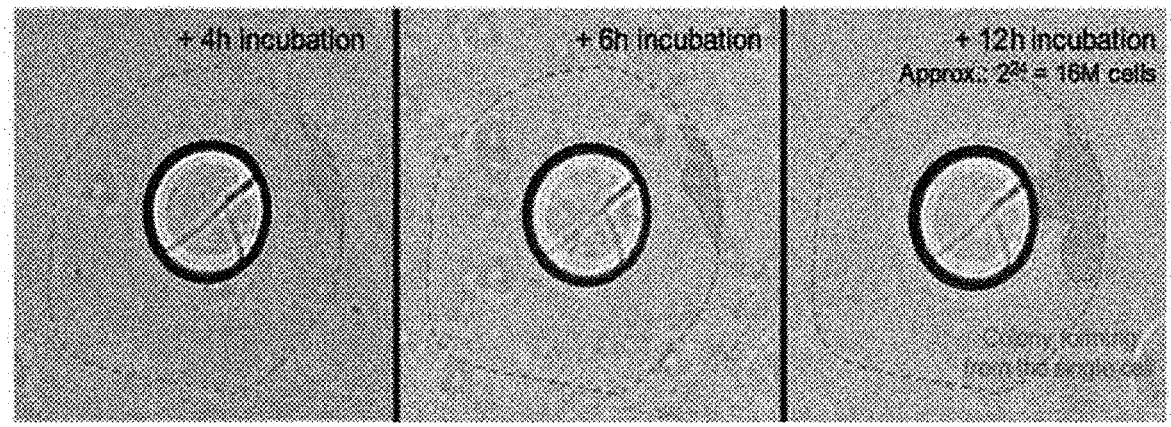
[Figure 6]
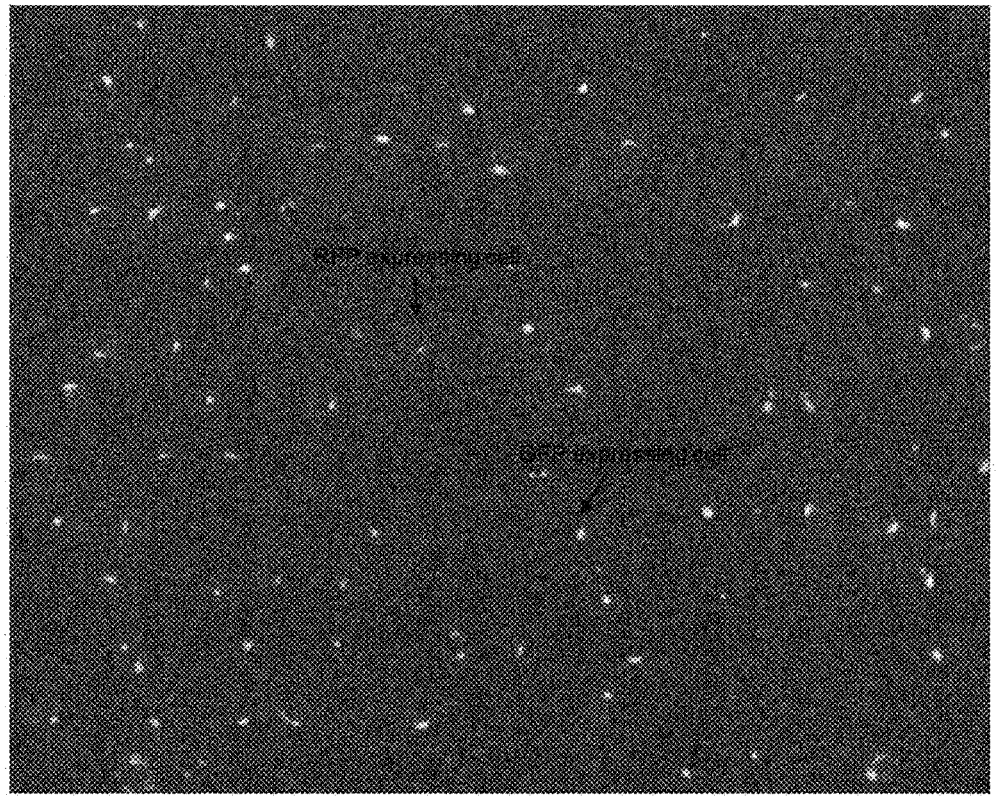

[Figure 7]
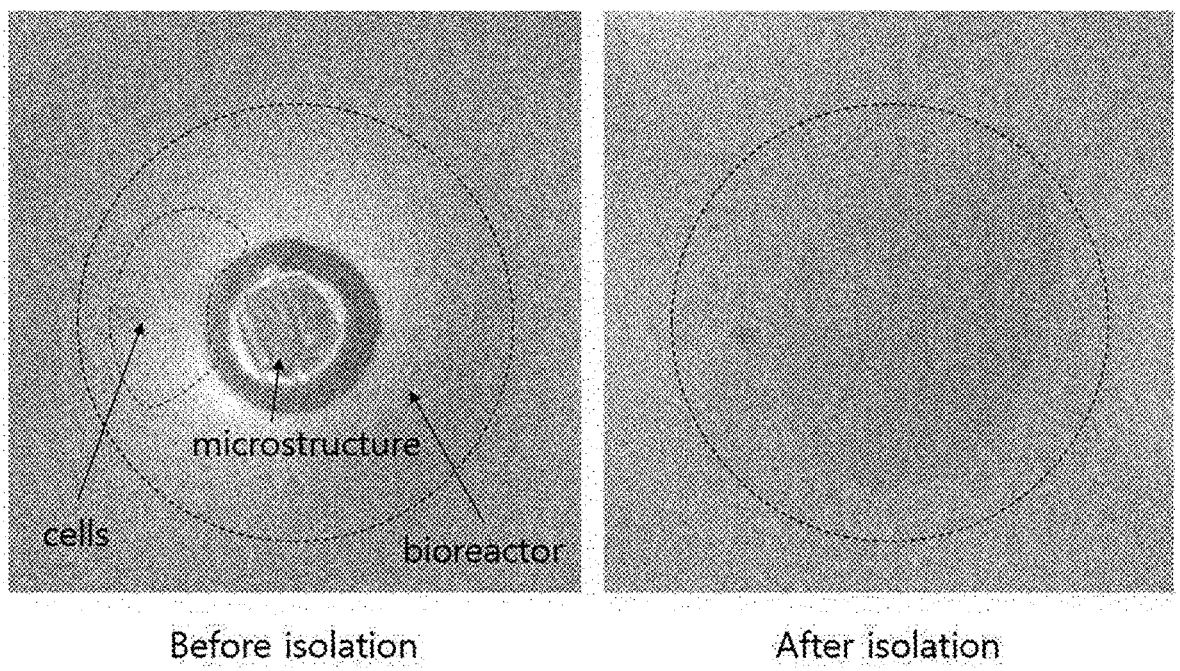
Before isolation — After isolation

[Figure 8]
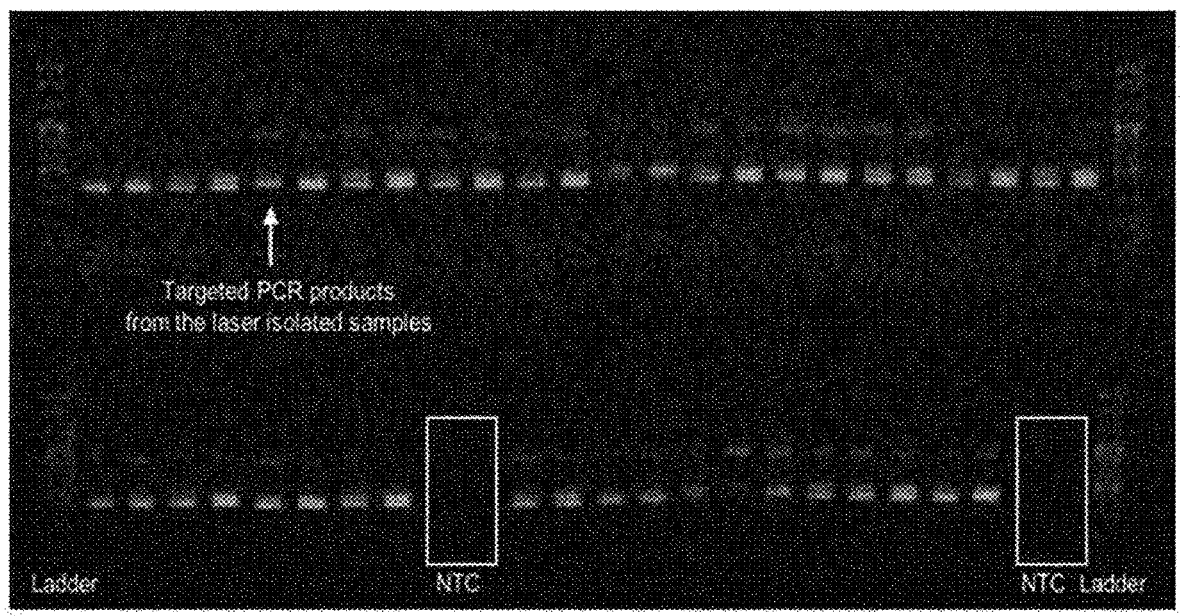

METHOD FOR ANALYSIS OF BIOSPECIMEN, ANALYSIS CHIP AND ANALYSIS SYSTEM BASED ON BIOREACTOR

CROSS-REFERENCE TO RELATED APPLICATIONS

This application is the U.S. National Phase under 35 U.S.C. § 371 of International Application No. PCT/KR2019/001588 filed on Feb. 8, 2019, which in turn claims the benefit of Korean Application No. 10-2018-0016125, filed on Feb. 9, 2018, the disclosures of which are incorporated by reference into the present application.

TECHNICAL FIELD

The present invention relates to a method of analyzing biological samples based on bioreactors, a chip for analyzing the biological samples, and a system for analyzing the biological samples, and more specifically, to a method related to analysis and retrieving the biological samples in bioreactors, and an analytical chip and an analytical system used therein.

BACKGROUND ART

Analysis of single organisms such as eukaryotic cells, prokaryotic cells, and viruses plays a very important role in fields such as biotechnology, medical, science, and the like. In particular, in the field of recent new drug development, efforts have been made to select antibodies that respond to specific antigens and efforts to find the amino acid sequence of proteins having high affinity for specific antigens as well as to find the amino acid sequence of antibodies physiologically reacting to antigens are included.

In general, in a method for analyzing an antibody that reacts to a specific antigen, a microorganism containing a DNA library is cultured on a solid medium in a spatially separated single state, and amplification of the DNA library in the microorganism is carried out through culture. Thereafter, colonies grown from a single microorganism are isolated, and analysis of the antibodies is carried out through Sanger sequencing, but the analysis of the amino acid sequence of a protein having a high antigen-specific affinity that is obtainable by the method as described above is enormously expensive and time consuming.

DISCLOSURE

Technical Problem

It is an object of the present invention to provide a technique capable of lowering the cost of isolating and analyzing a single colony and cultivating and extracting a colony having an antibody-specific DNA library at a rapid rate, as a method for overcoming the conventional technical limitations.

Technical Solution

According to an aspect of the present invention, there is provided a method of analyzing biological samples, including the steps of: introducing structures for assisting the formation of bioreactors on a substrate; providing a plurality of bioreactors on the substrate by forming the bioreactors holding the biological samples on the peripheral parts of each of the structures so as to contact each other in at least one region with the structures; and checking a change in the biological samples present in the bioreactors.

According to another aspect of the present invention, there is provided a chip for analyzing biological samples, including structures disposed in a separated state on a substrate; and bioreactors holding biological samples and disposed on the peripheral parts of each of the structures, wherein the bioreactors are formed to contact each other in at least one region with the structures by the interaction between the structures and the bioreactor-constituting materials.

According to still another aspect of the present invention, there is provided a system for analyzing biological samples, including: a chip for analyzing biological samples; a measurement tool for checking the physiological reaction of the biological samples present in bioreactors constituting the chip for analyzing the biological samples; and an extraction tool for extracting desired biological samples among the biological samples in which the physiological reaction has been checked, from a substrate, wherein the chip for analyzing biological samples comprises: structures disposed in a separated state on a substrate; and bioreactors holding biological samples and disposed on the peripheral parts of each of the structures, wherein the bioreactors are formed to contact each other in at least one region with the structures by the interaction between the structures and the bioreactor-constituting materials.

Advantageous Effects

The present invention relates to a method of culturing cells having a DNA library in bioreactors to form colonies, and extracting and culturing colonies having a high antigen-specific affinity as well as causing a physiological reaction. The work of analyzing the amino acid sequence of an antibody-specific DNA library has traditionally been carried out by an isolation method that requires enormous cost and time, called colony picking. In order to solve the problems of the conventional isolation method, automated equipment has been developed and introduced in the field of new drug development. In the case where this traditional method is used, when cells containing an antibody-specific DNA library having affinity against antigens filtered through screening are cultured on a solid medium, the integrity is low, as well as the throughput of retrieving the cultured cells is also very low. In addition, due to the characteristic of simply isolating the amplified cells, additional steps are needed to check whether the DNA library of the cultured cells actually has a high specific affinity or whether a physiological reaction occurs. The method of patterning the bioreactors where biological samples are retrievable and analyzable enables high-throughput analysis by introducing a method of extracting cells in a non-contact manner while simultaneously forming a highly integrated reactor. In addition, since it is possible to check and extract cells physiologically reacting to the antigens in the separated reactor space, the additional step of checking the affinity may be omitted, which has a great economic advantage compared to the existing technology. Therefore, the methods presented in the present invention may significantly reduce the time and cost required to analyze the amino acid sequence having an antigen-specific affinity as well as having a physiological reaction, and thus, it is expected to promote the development across fields such as new drugs, medicine, and biotechnology.

DESCRIPTION OF DRAWINGS

FIG. 1 is a process flowchart showing a method of analyzing an organism including biological samples using patterning of bioreactors according to an embodiment of the present invention.

FIG. 2(a), FIG. 2(b), FIG. 2(c) and FIG. 2(d) are a schematic view showing formation of structures for patterning bioreactors, patterning of bioreactors using the interaction between the structures and the bioreactor-constituting materials, checking of the physiological reaction of biological samples in bioreactors, and a process of retrieving biological samples in bioreactors according to an embodiment of the present invention.

FIG. 3 shows the results of the shape and arrangement of the pattern of bioreactors according to an embodiment of the present invention.

FIG. 4 is a schematic view showing a method of extracting biological samples in bioreactors according to an embodiment of the present invention.

FIG. 5 shows the results of culturing biological samples in bioreactors according to an embodiment of the present invention.

FIG. 6 shows the results of the physiological change of biological samples in bioreactors according to an embodiment of the present invention.

FIG. 7 shows the separation effect of biological samples under the presence or absence of a sacrificial layer according to an embodiment of the present invention.

FIG. 8 shows the results of DNA amplification of retrieved biological samples in bioreactors according to an embodiment of the present invention.

BEST MODE

In general, the analysis and retrieving the antibody library comprises the steps of: 1) culturing microorganisms such as *E. coli* containing the DNA library on a solid medium in a spatially separated state to form colonies, and 2) manually extracting the cultured colonies, 3) culturing the colonies or increasing the amount of the DNA library using a DNA amplification method such as PCR, and 4) checking whether the amplified DNA library-specific antibody in step 3) is actually physiologically reactive. The order of steps 3) and 4) may be changed. In comparison, the present invention relates to a method of amplifying a large number of DNA libraries at low cost, checking reaction thereof, and retrieving them, compared to the existing method, by fusion of patterning technology using the interaction between the structures and the bioreactor-constituting materials, structure formation technology for patterning bioreactors, technology for checking the reactivity of samples in bioreactors, and technology for extracting samples in bioreactors. This is due to the characteristics of the patterning technology using the interaction between the structures and the bioreactor-constituting materials and technology for extracting samples in bioreactors, and it is possible to analyze and extract samples at faster throughput and lower cost than the conventional method when extracting the DNA library colonies in which a physiological reaction was checked as in the present invention.

Hereinafter, examples of the present invention will be described in detail with reference to the drawings. The following examples are provided as examples to ensure that the ideas disclosed to those skilled in the art can be sufficiently conveyed. Therefore, the present invention is not limited to the examples described below and may be embodied in other forms. In addition, in the drawings, the width, length, thickness, and the like of components may be expressed in an exaggerated manner for convenience's sake. When explaining the drawings as a whole, it was described from the observer's point of view; and when one component is said to be on or "over" another component, this includes not only the case directly above the other component, but also the case where another component are in the middle.

FIG. 1 is a process flowchart showing a method of analyzing an organism including biological samples using patterning of bioreactors according to an embodiment of the present invention. The method of analyzing biological samples of the present invention will be described with reference to FIG. 1.

Patterning of bioreactors or structures for assisting it are formed on a substrate (step S1). The structures may be comprised of constituent materials of the substrate and may be formed of materials different from the constituent materials of the substrate. For example, the structures may be comprised of a polymer. The polymer may be any one or more selected from the group consisting of polystyrene, polycarbonate, cyclic olefin copolymer, polyethylene glycol-diacrylate (PEGDA), SU-8 photoresist (SU8), and polydimethylsiloxane (PDMS), as an example.

The size of each structure includes structures of any design that can be formed at least 1 μm in width, length, and height, respectively. The spacing between the structures may have a distance of 1 μm to 1 mm, preferably 10 μm to 100 μm.

The structures for patterning are arranged at specific intervals and may be formed through methods such as photo-lithograpy, contact lithograpy, heat curing, 3D printing, energy-beam (e-beam), a milling machine, and the like.

After forming the patterning of the bioreactors or structures for assisting it, patterns of bioreactors are formed on the substrate by forming the bioreactors holding the biological samples on the peripheral parts of each of the structures so as to contact each other in at least one region with the structures (step S2). The formation of the bioreactors may be carried out in a manner that introduces the bioreactor-constituting materials into the peripheral parts of each of the structures. More specifically, the formation of the bioreactors may be carried out in a manner that is formed on the substrate using self-assembly by the interaction between the structures and the materials constituting the bioreactors. Unless defined otherwise, the interaction refers to an interaction due to the surface properties of any one structure selected from the group consisting of hydrophilicity, hydrophobicity, and magnetism, or the properties of any one bioreactor-constituting material selected from the group consisting of viscosity, polarity, and magnetism. An example of the interaction may be a method of forming structures using polymers such as poly N-isopropylacrylamide (PNIPAM), polyacrylamide (PAM), poly 2-oxazoline, polyethylenimine (PEI), poly acrylic acid, poly methacrylate, poly ethylene glycol, poly ethylene oxide, poly vinyl alcohol (PVA), polyvinylpyrrolidone (PVP), polyelectrolytes, cucurbit[n]uril hydrate, and various miscellaneous hydrophilic polymers, which have strong hydrophilicity, and introducing the water-based bioreactor-constituting materials.

The bioreactors may be formed from a liquid material or a gel. The liquid material or the gel may comprise any one or more selected from the group consisting of a culture medium, a reaction buffer, and a solidifying agent. More preferably, it includes a probe. In addition, the solidifying agent may be a hydrogel as an example. When a probe is further included or a solidifying agent is included as described above, the step of selecting biological samples as described later may be more easily carried out.

The bioreactors may be physically connected or separated using a structure (three-dimensional design) change of the structures, a change in size of the structures, an adjustment of the spacing of the structures, or the interaction between the structures and the bioreactors, and the volume of the bioreactors may be adjusted through them. The volume of the bioreactors is not limited thereto, but may have a volume of at least 1 aL to 1 mL, preferably 1 fL to 10 uL, and more preferably 1 pL to 100 nL. The volume in the above range corresponds to the reaction volume that is the easiest for culturing microorganisms present in the bioreactors or post-processing such as analysis.

The structures used to constitute the bioreactors may be one or more, and more preferably, one structure constitutes one bioreactor. In this case, it is preferable because the bioreactors are formed in a physically separated state from each other so that the reaction may be carried out independently. In addition, it is preferable in view of the ease of adjusting the volume of the bioreactors, improving the integration of the bioreactors in the chip of the same area, the ease of image processing to locate the bioreactors, the ease of checking the change in the biological samples in the bioreactors, the ease of screening step on the chip utilizing the structures, and the increase in the efficiency of extracting the biological samples.

On the one hand, the method of introducing the biological samples into the bioreactors may be carried out in any one manner selected from i) a manner of mixing and loading the biological samples and the bioreactor-constituting materials, ii) a manner of adding the biological samples after formation of the bioreactors, and iii) a manner of adding the bioreactor-constituting materials after loading the biological samples. For example, as the step of introducing the biological samples into each bioreactor, a method of adding the biological samples to the patterned bioreactors may also be possible, but patterning may also be carried out by putting the biological samples in a liquid or a gel constituting the bioreactors.

The biological samples are not limited to an organism that may be included in the bioreactors provided according to the present invention, and may be any one or more selected from the group consisting of: any one microorganism selected from the group consisting of viruses, bacteria, fungi, algae, protozoa, parasitic pathogens, human or mammalian cells, and biofilms; any one biochemical molecule selected from the group consisting of nucleic acids, exosomes, viruses, and proteins; and a DNA library, as an example.

On the one hand, the number of microorganisms to be cultivated in a single bioreactor may be from at least a single cell to a large number of thousands of cells. In order to control the number of cells to be cultivated in a single bioreactor, the amount of cells to be put in a liquid (cell medium) or a gel containing the components necessary for culture may be adjusted, and the number of cells present in the bioreactors may be adjusted when patterning the bioreactors according to their concentration. Alternatively, cells may be introduced into the bioreactors using specific binding using affinity between cells and molecules or non-specific adsorption on the substrate.

After patterning the bioreactors, changes including physiological reaction of the biological samples present in the bioreactors are checked (step S3). The change in the biological samples means a change in amount or morphology due to growth, differentiation, outgrowth, death, and movement of the samples in the bioreactors; a change in bio-chemical properties due to products and constituents, including secretions; an expression of specific genes; and a reaction to specific molecules, including specific affinity for specific molecules in the samples, and the like. The physiological reaction may mean a label with a fluorescent material to the biological samples or a specific reaction of a material such as a protein and an enzyme. In addition, the check of the change in the biological samples may be carried out by observing the biological samples visually or using optical equipment.

The next step is a step that is carried out selectively, the change of the biological samples is checked and the selected desired specific biological samples are retrieved or extracted (step S4). The criteria and methods for selecting the specific samples are as follows: A method of simply culturing and selecting only samples containing a DNA library including selected genes through a screening process using antibiotics is used. In this case, only the information of whether or not the DNA library is included in the samples is simply provided, and usually the next step of re checking the physiological reactivity of the retrieved DNA library is required. In another method, a material having a specific affinity for a specific molecule on a product or surface of biological samples may be captured in the bioreactors, and the amount or the presence or absence of the captured material may be selected using a fluorescent molecule. In the method of capturing the specific molecule in the bioreactors, the molecule having affinity for the specific molecule may be coated on the surface of structures using a chemical method. In another method, an immobilizing agent (for example, hydrogel) may be used as a bioreactor-constituting material to fix a material having affinity for a specific molecule in the space of bioreactors. When the solidifying agent is used as a bioreactor-constituting material, it is possible to change the liquid material and maintain the bioreactors without losing or damaging the biological samples formed on the substrate even if another liquid material is additionally put thereinto. In particular, the bioreactors containing the solidifying agent has an advantage in that the additional reaction of the biological samples may be further checked because the biological samples are fixed and do not flow down by the liquid material even when the liquid material is additionally put thereinto.

On the one hand, the bioreactors may be formed from a constituting material including a liquid material or a gel, and the bioreactors may further include a probe capable of detecting a change in cells. As an example, it is possible to selectively classify and separate samples by including probes for selecting specific biological samples, such as fluorescent dyes and beads. Specifically, when the probes are mixed and loaded together with the cells at the same time, it is possible to distinguish the cells expressing the desired specific material on the chip using the probes first loaded together with samples without additionally loading fluorescent dyes.

In addition, when the bioreactors are formed from a constituting material containing a solidifying agent, the desired specific materials expressed in biological samples may be captured in the bioreactors. As an example, specific antibodies secreted from cells in the matrix may be immobilized to check antibody secretion. In addition, it is possible to change the bioreactor-constituting materials to check a change in the biological samples without losing or damaging the biological samples. Specifically, since the biological samples loaded on the substrate are fixed by the solidifying agent, the materials constituting bioreactors may be added or changed, by loading bioreactor-constituting materials and the biological samples on the substrate, and then further adding the material constituting the bioreactors (liquid sample, buffer, reaction solution, and the like) according to the purpose.

On the one hand, the substrate may be selected from the group consisting of a substrate replicated from a template, a substrate including a sacrificial layer therein, a substrate coated with a sacrificial layer on the surface, a substrate undergoing a phase transition by the electromagnetic field, and a substrate capable of absorbing the energy of the electromagnetic field. The substrates have an advantage in that their efficiency may be increased when energy is applied in the extraction step. The sacrificial layer may be glass that has increased the absorption of energy by reducing the transmittance or increasing the absorbance, or may be silicone that has increased the absorption of energy by reducing the transmittance or increasing the absorbance. In addition, the sacrificial layer may be coated on a solid surface such as glass or silicone, or may be present inside a solid such as glass or silicone, but is not limited thereto. In addition, the substrate undergoing a phase transition by the electromagnetic field means a substrate in which the solid substrate is liquefied, vaporized, or plasmaized temporarily or permanently by the electromagnetic field. In addition, the substrate capable of absorbing the energy of the electromagnetic field means a substrate capable of reacting to the application of the electromagnetic field and being separated by including fine particles and the like having magnetic properties inside the substrate to efficiently absorb the energy of the electromagnetic field.

Preferably, a sacrificial layer is placed on the substrate. The sacrificial layer absorbs energy, thereby increasing extraction efficiency while reducing the total amount of energy applied to the biological samples, which can minimize damage to the biological samples due to the applied energy. More preferably, the structures are patterned on the substrate including the sacrificial layer. As an example, the substrate used in FIGS. 3 to 5 corresponds to an example of use of a glass substrate in which the sacrificial layer is included in the form of a coating layer, and it was checked that the technology for patterning a micro-scale structure was effectively implemented on the glass substrate on which the sacrificial layer is coated through the corresponding drawings.

In addition, the structures may be composed of a material undergoing a phase transition in the same manner as the substrate, and a sacrificial layer may be placed on the structures in the same manner as the substrate. In addition, a chemical surface treatment may be applied to the structures to retrieve specific samples in the bioreactors.

In addition, it is possible to amplify the amount of the biological samples in the bioreactors through methods such as division of microorganisms and amplification of DNA molecules. From the above, even if the sacrificial layer is not present, it is possible to minimize damage occurring in the process of extracting the biological samples.

The desired specific samples are extracted from the substrate by applying energy to the desired samples among the samples in the bioreactors in a non-contact manner. The method of applying energy in a non-contact manner may be one or more manners selected from the group consisting of a micro-manipulator, an ultrasonic wave, a pneumatic pressure, and a laser. The non-contact manner does not cause a problem of cross contamination and minimizes the use of consumables, and thus also has an advantage in terms of cost.

Preferably, pulse laser ablation or radiation pressure ejection may occur due to the incident of the pulse laser in the non-contact manner. In this case, a part or all of the samples in the bioreactors located on the substrate are separated from the substrate, and may be easier to retrieve since the progressing direction of the laser wavelength and the moving direction of the samples are not significantly different.

The pulse laser may have a wavelength of 10 to 10,000 nm, preferably 20 to 5,000 nm, more preferably 100 to 2,000 nm. In the above range including the visible light region or the infrared region, the electromagnetic field does not significantly affect the optical component and may transmit sufficient energy to the substrate or the biological samples. In addition, since most commercial pulse lasers operate in the above range, it is easy to implement a system, and even when a substrate using a sacrificial layer is used, the present invention may be practiced without major changes to the system.

The pulse laser may have a pulse duration of 1 as to 1 ms, preferably 1 fs to 100 ns. The pulse duration has an advantage in that when the pulse laser ablation due to the pulse laser occurs, the progressing paths of the separated substrates and the samples are more constant, and thus they are easier to be retrieved. On the one hand, the output of the pulse laser may be 10 to 1 $kJ/cm^2$ per pulse, preferably 100 to 300 $kJ/cm^2$ per pulse. When the pulse laser ablation due to the pulse laser occurs in the pulse duration and the output, the samples in the bioreactors may be less damaged, which may bring high efficiency when performing the post-processing process of the separated and retrieved samples.

The step of separating the desired biological samples from the substrate includes a process of transferring the desired biological samples to a reservoir. The transfer to the reservoir is a process required for use when culture and storage of the separated samples or reaction with other reactants is required. The reservoir may include a container manufactured for the purpose of causing or observing a physical or chemical reaction. In addition, the reservoir may include a container manufactured for storage of biochemical molecules. The reservoir has a volume of 1 aL to 1 L, preferably 1 fL to 10 mL, and more preferably 1 pL to 500 uL, which corresponds to the reaction volume that is the easiest for culture of separated samples in the bioreactors and various post-processing after checking physiological reactivity. In addition, the reservoir may be, for example, an array structure of microwells having a volume of each well of 1 pL to 1 uL (David K. Wood et al., Single cell trapping and DNA damage analysis using microwell arrays, PNAS (2010)), which is to minimize the waste of reagents by reducing the reaction volume during various post-processing such as culture of the separated samples or polymerase chain reaction (PCR), rolling circle amplification (RCA), multiple displacement amplification (MDA), and the like. In addition, from the above, some reactions may be expected to improve the reaction rate or efficiency.

The step of separating the desired samples from the substrate is carried out in a manner that transfers a part or all of the samples to one or more reservoirs. Since the act of separating a part of the samples enables the corresponding samples to be used more than once, it is possible to apply a method of grasping the location of the previously extracted samples and retrieving them immediately when the same sample is needed later. In addition, a plurality of the desired samples may be separated into a single reservoir, which may induce a physiological reaction between several samples.

For extraction of the samples, the extraction tool may be combined or linked with equipment capable of image observation and storage. In addition, an object recognition algorithm that analyzes the image to grasp the shape and position of the samples may be used in a form combined with a drivable computing device.

The extraction tool used for the extraction of the biological samples may be combined with a device for position movement. The device for the position movement may be a transmission device and may have a precision that may be operated in a fine range of preferably 1 mm or less, more preferably 100 μm or less, and even more preferably 5 μm or less. Since the spacing between the spots of most microarrays is 5 μm to 100 μm, the transmission device having a precision that may be operated in a fine range of particularly 5 μm or less enables accurate separation of the desired samples in most microarrays.

FIG. 2 is a schematic view showing formation of structures for patterning bioreactors, patterning of bioreactors using the interaction between the structures and the bioreactor constituent materials, checking of physiological reactivity of biological samples in the bioreactors, and a process of retrieving biological samples in the bioreactors according to an embodiment of the present invention. FIG. 2(a) shows the structures formed on the substrate. FIG. 2(b) shows a process in which the bioreactors are patterned due to the interaction between the structures formed in the process (a) and the materials constituting the bioreactors. FIG. 2(c) shows a process of checking the change including the physiological reaction of microorganisms cultured in the bioreactors. FIG. 2(d) shows a process of extracting samples in the bioreactors to be separated from the substrate and transferring them to a storage and culture vessel.

FIG. 3 shows the results of the patterning of the bioreactors according to an embodiment of the present invention. The results of the patterning of the bioreactors in the present invention form PEGDA structures (corresponding to the structure mark in the drawing) using photo-lithography to pattern the bioreactors on a glass substrate. Subsequently, the bioreactors (corresponding to the bioreactor mark in the drawing) are created around the structures due to the interaction of the cell culture medium material constituting the bioreactor and the PEGDA structures on the glass substrate, thereby forming physically separated patterns of the bioreactors. The results of the patterning of the bioreactors thus formed may be utilized as a chip for analyzing the biological samples.

According to the embodiment of the present invention, the adjustment of the spacing between the structures patterned on the substrate is possible at a resolution level of up to 1 μm. That is, it is possible to pattern structures having all numerical intervals of 1 μm or more. In view of the convenience of biological sample analysis, the accuracy of biological sample analysis, and the convenience in the selective extraction of biological samples, it is preferable that the spacing between structures is great. However, since the greater the spacing between structures, the lower the degree of integration of the bioreactors in the chip, it is desirable that in view of the convenience of biological sample analysis, the accuracy of biological sample analysis, the convenience in the selective extraction of biological samples, and the degree of integration of biological samples in the chip, the spacing between structures is 10 μm to 1 mm.

The bioreactors may be formed from a liquid material or a gel, the biological samples may be any one or more selected from the group consisting of: any one microorganism selected from the group consisting of viruses, bacteria, fungi, algae, protozoa, parasitic pathogens, human or mammalian cells, and biofilms; any one biochemical molecule selected from the group consisting of nucleic acids, exosomes, viruses, and proteins; and a DNA library, and descriptions related to these are replaced with the specific descriptions presented previously and descriptions thereof will be omitted below.

FIG. 4 is a schematic view showing a method of extracting biological samples according to an embodiment of the present invention. A stage equipped with a substrate on which a plurality of bioreactors are formed; an extraction device for applying energy in a non-contact manner to separate the desired samples in the bioreactors from the substrate; and a control device for positioning a specific region of the substrate to correspond to the extraction device in order to separate the desired samples are included.

According to the embodiment of the present invention, the substrate used in FIG. 4 corresponds to an example of use of a glass substrate in which the sacrificial layer is included in the form of a coating layer, and it was checked that the technology for patterning a micro-scale structure was effectively implemented on the glass substrate on which the sacrificial layer is coated through the corresponding drawings.

According to an embodiment, the extraction device may include a pulse laser light source and a condenser. The condenser may preferably be an optical lens because this may be used for the purpose of concentration of pulse laser energy, and at the same time, may be also used for observation of the molecular clone and substrate. The pulse laser may be accurately irradiated to the position of the biological samples to be separated on the substrate at a desired time point, which is generally carried out by controlling the pulse laser with a control device such as a computer. The optical lens may be an optical lens having a magnification of 2× to 100×, preferably 10× to 40×. This magnification has an advantage that a suitable separable energy may be transferred on the substrate, and at the same time, the distance between the lens and the microarray substrate is too close to prevent contact with each other or out of the focus length.

According to an embodiment, at least one of the stage, the extraction device, and the control device in the extraction system of the biological samples has a precision that may be operated in a fine range of 1 mm, preferably 100 μm, more preferably 1 μm or less. Since the spacing between most biological samples is 1 μm or more, the stage, the extraction device, and the control device having a precision that may be operated in a fine range of 1 μm or less may enable accurate separation of desired biological samples from most substrates.

According to an embodiment, the system may further include an imaging device for observing the substrate to separate the desired biological samples. The imaging device may be comprised of one or more of an optical lens, a light source, and an image sensor. The optical lens may be an optical lens included in the extraction device, or a separate optical lens may be additionally used, if necessary.

The wavelength of the light source may have a wavelength of 10 nm to 10,000 nm, preferably 50 nm to 2,000 nm, more preferably 100 nm to 1,500 nm, and observation or measurement of the substrate using fluorescence or visible light in the corresponding wavelength region may be the easiest. As the light source, for example, a halogen lamp may be used.

The image sensor generally uses a charge-coupled device (CCD), but is not limited thereto. The imaging device may be used in the step S3 to obtain a position of an individual spot in which the desired samples among samples in reactors on the substrate is located, and then to check whether the spot is present at the position. In addition, the imaging device may be used in the step S3 to check whether an extraction tool for applying energy is accurately positioned to enable separation of the desired biological samples according to the location information. In addition, the imaging device may be used in the step S4 to check whether the desired biological samples separated from the substrate are present in the reservoir.

According to an embodiment, a separate stage equipped with a reservoir for retrieving the separated desired biological samples may be further included. The stage may have a precision that may be operated in a fine range of 1 mm or less, preferably 100 µm or less, and more preferably 1 µm or less. A separate stage equipped with the reservoir may facilitate utilization of the separated samples, and a stage having a precision of 1 µm or less may enable separation of the samples into a reservoir having an array structure of microwells having a volume of each well of 1 pL to 1 uL.

According to an embodiment of the present invention, a chip for analyzing biological samples; a measurement tool for checking the physiological reaction of the biological samples present in the bioreactors constituting the chip for analyzing the biological samples; and an extraction tool for extracting the desired biological sample among the biological samples in which the physiological reaction has been checked, from a substrate, are included, wherein the chip for analyzing biological samples comprises: structures disposed in a separated state on the substrate; and bioreactors holding the biological samples and disposed on the peripheral parts of each of the structures, and wherein the bioreactors may be formed to contact each other in at least one region with the structures by the interaction between the structures and the bioreactor-constituting materials.

FIG. 4 is an embodiment of a system for extracting or analyzing the biological samples according to an embodiment of the present invention, and the entire system is largely divided into an upper system and a lower system. The upper system is computer-controlled and is comprised of an upper stage (motorized XY stage) with a substrate attached downward, an energy applying device, and an upper imaging device.

According to an embodiment, the pulse laser beam condensed through the condensing device is incident on the substrate and extracts biological samples on the substrate by expansion pressure or radiation pressure by pulse laser ablation, and pushes them to a cell culture or PCR plate serving as a storage and culture vessel at the bottom. The condenser may be an optical lens, and may be, for example, an optical lens having a magnification of 2× to 100×. A PCR tube rack or PCR plate serving as a reservoir is attached upward in the lower system, which is comprised of a lower stage (motorized XYZ stage) and a lower imaging device that may move to the Z axis. In the lower imaging device, a reservoir capable of transmission imaging may be used to optically check whether the biological samples separated from the substrate are collected or to determine a physical reference position of the well. The reservoir includes various types of receiving tools including, for example, a flat bottom reservoir made of transparent plastic or a flat bottom PCR plate. The flat bottom of the reservoir has an advantage that imaging may be facilitated by reducing the influence on the path of light from the light source of the lower imaging device.

FIG. 5 shows the results of culturing samples in the bioreactors according to an embodiment of the present invention. The bioreactors are formed by mixing the cell culture medium(LB medium) constituting the bioreactors with E. coli to be cultured, and then loading the mixture on a chip. Thereafter, cells loaded on the chip are cultured in the bioreactors and, over time, continue to grow from a single cell and form colonies.

FIG. 6 shows the results of checking the physiological reactivity of samples in the bioreactors according to the embodiment of the present invention. Cells to be introduced into the bioreactors are divided into E. coli, which includes a selection marker and a library of red fluorescent protein (RFP) or green fluorescent protein (GFP), and cells, which do not include the both. Only cells to be grown by selection markers such as ampicillin and kanamycin contained in the liquid/gel component constituting the bioreactors will grow in the bioreactors around the structures, thereby allowing the physiological reactivity of the samples in the bioreactors to be checked.

FIG. 7 shows the separation effect of biological samples under the presence or absence of a sacrificial layer according to an embodiment of the present invention. After the ITO is coated or deposited to make the sacrificial layer on the glass substrate, structures (corresponding to microstructure mark in the drawing) for forming bioreactors are formed thereon using photo-lithography. As an example of separating the cells formed in the bioreactors using a non-contact pulse laser separation manner, when the laser energy is irradiated to the ITO sacrificial layer on the substrate, a part or all of the bioreactors, cells, and structures on the chip may be freely separated. Using a non-contact pulse laser, samples in each bioreactor may be retrieved to each reservoir. When the sacrificial layer is not included, no matter how high energy the laser is irradiated onto the substrate, there is no reaction or separation in the bioreactors or samples.

FIG. 8 shows the results of DNA amplification of retrieved samples in the bioreactors according to an embodiment of the present invention. Cells grown or selected in the bioreactors are separated on the chip using a non-contact pulse laser separation manner, and each sample may be moved to each reservoir. E. coli samples separated on a chip may be used to amplify DNA (targeted PCR products from the laser isolated samples in the drawing) of desired regions of each sample through a PCR reaction.

The invention claimed is:

1. A method of analyzing biological samples, comprising the steps of:
   providing a substrate;
   introducing structures for assisting formation of bioreactors on the substrate;
   providing a plurality of bioreactors on the substrate by forming the bioreactors on peripheral parts of each of the structures such that the bioreactors contact the structures, wherein the bioreactors hold biological samples; and
   checking a change in the biological samples present in the bioreactors.

2. The method of analyzing biological samples according to claim 1, wherein the bioreactors are formed from a bioreactor-constituting material, wherein the bioreactor-constituting material is a liquid material or a gel.

3. The method of analyzing biological samples according to claim 2, wherein the liquid material or the gel comprises any one or more selected from the group consisting of a culture medium, a reaction buffer, and a solidifying agent.

4. The method of analyzing biological samples according to claim 3, wherein the bioreactors comprise the solidifying agent and the solidifying agent is capable of adding or changing the bioreactor-constituting materials without losing or damaging the biological samples in the bioreactors.

5. The method of analyzing biological samples according to claim 2, wherein the formation of the bioreactors uses self-assembly by the interaction between the structures and the bioreactor-constituting materials.

6. The method of analyzing biological samples according to claim 2, wherein the volume of the bioreactors is adjusted using a structure change of the structures, a change in size of the structures, an adjustment of the spacing of the structures, or the interaction between the structures and the bioreactor-constituting materials.

7. The method of analyzing biological samples according to claim 5, wherein the interaction is due to the surface properties of any one structure selected from the group consisting of hydrophilicity, hydrophobicity, and magnetism, or the properties of any one bioreactor-constituting material selected from the group consisting of viscosity, polarity, and magnetism.

8. The method of analyzing biological samples according to claim 1, wherein the bioreactors are formed in a physically separated state from each other.

9. The method of analyzing biological samples according to claim 1, which is carried out in any one manner selected from i) a manner of mixing and loading the biological samples and the bioreactor-constituting materials, ii) a manner of adding the biological samples after formation of the bioreactors, and iii) a manner of adding the bioreactor-constituting materials after loading the biological samples in order to introduce the biological samples into the bioreactors.

10. The method of analyzing biological samples according to claim 1, wherein the change in the biological samples is any one or more selected from the group consisting of: a change in amount or morphology due to growth, differentiation, outgrowth, death, and movement of the biological samples; a change in biochemical properties due to products and constituents, including secretions; a reaction to specific molecules, including specific binding to specific molecules; and an expression of specific genes.

11. The method of analyzing biological samples according to claim 10, wherein the checking of the change in the biological samples is carried out by observing visually or with optical equipment.

12. The method of analyzing biological samples according to claim 1, further comprising a step of extracting only desired biological samples among the biological samples from the substrate.

13. The method of analyzing biological samples according to claim 12, wherein the step of extracting the desired biological samples from the substrate is carried out by any one or more selected from the group consisting of a micromanipulator, an ultrasonic wave, a pneumatic pressure, and a laser.

14. The method of analyzing biological samples according to claim 1, wherein the biological samples are any one or more selected from the group consisting of: any one microorganism selected from the group consisting of viruses, bacteria, fungi, algae, protozoa, parasitic pathogens, human or mammalian cells, and biofilms; any one biochemical molecule selected from the group consisting of nucleic acids, exosomes, viruses, and proteins; and a DNA library.

15. The method of analyzing biological samples according to claim 1, wherein the substrate is any one selected from the group consisting of a substrate replicated from a template, a substrate including a sacrificial layer therein, a substrate coated with a sacrificial layer on the surface, a substrate undergoing phase transition by the electromagnetic field, and a substrate capable of absorbing the energy of the electromagnetic field.

16. The method of analyzing biological samples according to claim 1, in the step of introducing the structures, the structures are patterned on the substrate such that the structures are arranged two-dimensionally at a specific interval.

17. The method of analyzing biological samples according to claim 1, in the step of providing the bioreactors, the bioreactors directly contact the substrate and the structures.

18. The method of analyzing biological samples according to claim 1, in the step of providing the bioreactors, the bioreactors are physically separated from one another, each of the bioreactors contacts only the corresponding structure among the structures and contacts the substrate.

19. The method of analyzing biological samples according to claim 12, wherein the step of extracting the desired biological samples among the biological samples from the substrate is carried out by a pulsed laser.

* * * * *